United States Patent
Similowski et al.

(10) Patent No.: US 11,110,252 B2
(45) Date of Patent: Sep. 7, 2021

(54) DEVICE FOR PROTECTING AND HOLDING IN POSITION A PROBE THAT IS INTENDED TO BE PLACED INSIDE THE BODY OF A PATIENT IN COMMUNICATION WITH THE OUTSIDE

(71) Applicants: MMG, Les Aires (FR); UNIVERSITE PIERRE ET MARIE CURIE (PARIS 6), Paris (FR)

(72) Inventors: Thomas Similowski, Issy-les-moulineaux (FR); Serge Renaux, Les Aires (FR)

(73) Assignees: MMG, Les Aires (FR); UNIVERSITE PIERRE ET MARIE CURIE (PARIS 6), Paris (FR)

(*) Notice: Subject to any disclaimer, the term of this patent is extended or adjusted under 35 U.S.C. 154(b) by 332 days.

(21) Appl. No.: 15/569,962

(22) PCT Filed: Apr. 29, 2016

(86) PCT No.: PCT/IB2016/052451
§ 371 (c)(1),
(2) Date: Oct. 31, 2017

(87) PCT Pub. No.: WO2016/174632
PCT Pub. Date: Nov. 3, 2016

(65) Prior Publication Data
US 2018/0154116 A1   Jun. 7, 2018

(30) Foreign Application Priority Data
Apr. 30, 2015 (FR) .................................. 1553948

(51) Int. Cl.
*A61M 25/02* (2006.01)
*A61M 16/04* (2006.01)

(52) U.S. Cl.
CPC ........ *A61M 25/02* (2013.01); *A61M 16/0497* (2013.01); *A61M 2025/024* (2013.01);
(Continued)

(58) Field of Classification Search
CPC ........ A61M 16/0497; A61M 2025/002; A61M 2025/0213; A61M 2025/028; A61M 2025/0293; A61M 25/04; A61M 2025/022
See application file for complete search history.

(56) References Cited

U.S. PATENT DOCUMENTS 4,270,529 A    6/1981  Muto
4,699,616 A *  10/1987 Nowak ................. A61M 25/02
                                              128/DIG. 26
(Continued)

FOREIGN PATENT DOCUMENTS

DE       202006001328      4/2006

*Primary Examiner* — Nathan R Price
*Assistant Examiner* — Tasnim Mehjabin Ahmed
(74) *Attorney, Agent, or Firm* — Lex IP Meister, PLLC

(57) ABSTRACT

Device (100) for holding in position a probe for placing the inside of a patient's body in communication with the outside, characterized in that it comprises, arranged along a longitudinal axis (X-X') of the device: at its distal end, a means (110) of supporting the device on the patient's body and that extends radially, comprising an axial opening (114) for the passage of said probe and comprising a first radial opening (111) communicating with the said axial opening, at its proximal end, a means (120) of guiding said probe comprising a second radial opening (121), a means (130) of spacing said bearing means and said guide means apart longitudinally.

23 Claims, 5 Drawing Sheets

(52) U.S. Cl.
CPC ............... *A61M 2025/028* (2013.01); *A61M 2025/0233* (2013.01); *A61M 2207/00* (2013.01)

(56) References Cited

U.S. PATENT DOCUMENTS

| | | | | |
|---|---|---|---|---|
| 4,832,019 A * | 5/1989 | Weinstein | ......... | A61M 16/0488 128/207.17 |
| 5,352,211 A * | 10/1994 | Merskelly | ............. | A61M 25/02 128/DIG. 26 |
| 8,636,008 B2 * | 1/2014 | Flory | ................ | A61M 16/0488 128/207.14 |
| 2008/0202529 A1 * | 8/2008 | Flory | ................ | A61M 16/0488 128/207.17 |
| 2014/0332009 A1 * | 11/2014 | Haider | .............. | A61M 16/0493 128/207.17 |

* cited by examiner

DEVICE FOR PROTECTING AND HOLDING IN POSITION A PROBE THAT IS INTENDED TO BE PLACED INSIDE THE BODY OF A PATIENT IN COMMUNICATION WITH THE OUTSIDE

The invention falls within the field of devices to assist with the placement and maintenance of a probe, intended to place the inside of a patient's body in communication with the outside.

In the medical field, it is common to have to place the inside of a patient's body in communication with a device adapted to the care to be given, for example an aspiration system or an artificial ventilation system.

Probe-assisted artificial ventilation is the vital assistance measure most frequently used in emergency situations and resuscitation. It may be administered using different "interfaces" between the patient and the ventilator. Tracheal intubation constitutes one of these interfaces, preferred in the most serious situations, or when the patient's condition requires sedation. It consists of introducing a probe into the air pathways: the distal end of the probe is placed in the trachea; its proximal end is connected to the ventilator. Although tracheal intubation can be done using a nasal approach or a buccal approach, the buccal approach is currently almost exclusively used in practice.

Once the probe is placed, it is necessary to fasten it and protect it from being bitten by the patient. These two objectives are crucial for the quality of ventilation assistance: a probe that moves may make the latter ineffective or dangerous (outward movement or extubation: absence of ventilation; inward movement: risk of so-called "selective" intubation leading to no longer ventilating both lungs, but instead only one). A probe that has been bitten or bent may make ventilation ineffective, if not impossible.

The orotracheal intubation probes can be fastened in different ways:
  It is possible to use, for this purpose, a simple cord laced on the probe, optionally protected by a plastic sheath; the cord does not provide perfect fastening of the probe, and no protection; furthermore, having to be tightened around the patient's head, it may cause discomfort and lesions (sores at friction points, such as the labial angle or the ears);
  It is possible to add, to the cord, a so-called "Guedel" intra-buccal canula that adds discomfort to the presence of the probe in the mouth.

It should be noted that beyond the need to fasten and protect the intubation probe, care for ventilated patients sometimes involves the need to mobilize it, to optimize its position after accidental movement of any origin (spontaneous, detected by a systematic inspection; accidental, by the patient or caregiving staff during movement, transport or care; procedural, for example during bronchial endoscopy). Furthermore, preventing nosocomial infections and ensuring patient comfort involve mouth care in patients ventilated and intubated through the mouth multiple times a day. The quality of this care requires easy access to the entire buccal cavity, and therefore sometimes freeing the probe. Having to remove and replace an intubation probe fastening device therefore presents a risk, as well as work time. The current devices, in particular a cord, do not make this task easy. It must be recalled that both ends of the probe are engaged: the distal end in the trachea of the patient (where a low-pressure balloon inflatable from the outside using a small coupling ensures sealing), the proximal end being connected to the ventilator. A probe maintenance and protection device must be able to be fastened on the probe and removed without passing through an end (and therefore in particular without having to disconnect the probe from the ventilator). With the devices of the state of the art, this operation requires using both hands, or even two people.

The present invention aims to provide a device that can be fastened and attached with one hand relative to a probe whereof both ends are engaged, one of which is located inside the patient's body, and which ensures effective maintenance and protection for this probe. It is in fact important to avoid any movement of this probe that could cause serious bodily injury to the patient.

To that end, the invention proposes a device for maintaining a probe placing the inside of a patient's body in communication with the outside, characterized in that it comprises, arranged along a longitudinal axis of the device:
  at its distal end, bearing means of the device on the patient's body that extend radially, including an axial opening for the passage of said probe and including a first radial opening communicating with said axial opening,
  at its proximal end, guide means for said probe including a second radial opening,
  longitudinal separating means for said bearing means and said guide means.

Throughout the text, a "distal" element will refer to an element, for example an end, a face, etc., oriented toward the patient during use, and a "proximal" element will refer to an element oriented away from the patient during use.

For the placement of the device on the probe, the latter is made to penetrate through the radial openings arranged both in the bearing means and in the guide means; the probe is then positioned along the axis X-X' of the device, without it being necessary to mobilize either of the ends of the probe. The device detaches from the probe through the reverse maneuver.

The probe is for example an orotracheal probe or any other probe placing the inside of a patient's body in communication with the outside, their shared characteristic being that both ends of this probe are not able to be mobilized, i.e., the device cannot be slid onto the probe. The width of the openings allows probes with a wide variety of diameters to pass, by acting on the plasticity of the probes generally used.

The bearing means is intended to come into contact with the patient's lips or skin; its radial extension depends on the application. It for example assumes the form of a corolla able to include fastening elements, for example openings, for a cord intended to fasten the device on the patient's body.

The function of the guide means is to maintain the probe along the longitudinal axis of the device, at least over the length of the device. It advantageously assumes the form of a coaxial ring, preferably, but non-limitingly, toroidal.

The function of the separating means is simply to keep the bearing means and the guide means separated. It for example assumes the form of a plate, rectilinear or curved, the length of which also depends on the application.

The invention proposes two alternative embodiments regarding the radial openings:
  In a first variant, the first radial opening and the second radial opening are substantially diametrically opposite relative to the longitudinal axis of the device; this alternative is preferred because it avoids accidental separation of the probe and the device,
  In a second variant, the first radial opening and the second radial opening are situated on the same side relative to the longitudinal axis of the device.

The device may further have one or another of the following additional features, alone or in combination:

In an application to the fastening of an orotracheal probe, the bearing means can be extended over its distal face by a coaxial cylindrical body including a longitudinal slit, said slit being in communication with the radial opening of the bearing means.

This cylindrical body protects the probe from being bitten by the patient when the device is in place. Its longitudinal slit, in communication with the first radial opening arranged on the bearing means and substantially with the same extension, makes it possible to place the device on the probe and remove it easily.

Advantageously, the guide means may include a protuberance that extends radially in the direction opposite the separating part.

Advantageously, the guide means may include a tongue that extends radially from the protuberance.

The device may further include a blocking means provided to block the probe against the separating means when said probe extends along the longitudinal axis of the device.

This frictional blocking means prevents relative slipping of the probe and the device, and therefore thus prevents the probe from escaping from the patient's body or penetrating the latter too deeply.

The blocking means may include a strip that extends longitudinally from the proximal face of the bearing means, diametrically opposite the separating means.

This strip is thin enough to be deformed elastically, such that its proximal end can come closer to or move away from the longitudinal axis of the device.

Advantageously, the strip may assume a radially curved shape and include a blocking part that extends toward the longitudinal axis of the device, so as to block the probe between said blocking part and the separating means when force is exerted on said strip.

This strip is not rectilinear, but has a wave shape, a "wave trough" shape being closer to the longitudinal axis of the device. The strip and the plate of the separating means form an elastic clamp that makes it possible to block the probe and prevent it from slipping inside the device without crushing the probe. The aim is in fact not to interrupt the flow of gas or liquid in the probe, but only to block it by friction. To that end, the part of the plate located across from the strip is smooth, and has no overthickness or boss that would contribute to this crushing.

Advantageously, the inner face of the separating means can be provided with a nonslip layer.

Advantageously, the device may further include nonreturn means preventing the return of the blocking means into the position where the blocking part is brought closer to the separating part and therefore in which the probe is blocked in the device.

In this position, the probe, which passes along the longitudinal axis of the device, is blocked against the separating means. The nonreturn means keeps the strip and its blocking part against the probe. The separating means is more rigid than the strip, such that when the strip is pressed against the probe and the probe against the separating means, it is the strip that deforms.

Advantageously, the nonreturn means may include a notched surface on a distal face of the protuberance, said notches being provided to cooperate with a tooth situated at the proximal end of the blocking means.

The longitudinal extension of the strip is substantially equal to that of the separating means, such that its proximal end can cooperate with a series of notches provided on a distal face of the guide means. The end of the strip is freed from the notches by exerting a force on the tongue tending to separate this tongue from the bearing means.

Advantageously, the device may be in a single piece.

The device is then made in a single piece; it does not require any assembly of different parts that slide relative to one another, or are screwed relative to one another.

The device can be made from a plastic for pharmaceutical or medical-surgical use.

These plastics intrinsically have a certain plasticity, a higher rigidity of an element being obtained when its compactness is increased, for example its thickness. Thus, the plate making up the separating means has a larger transverse extension than the strip of the blocking means, so as to be more rigid than the strip. Likewise, when the device includes a cylindrical body intended to protect the probe from being bitten, the thickness of the wall of the cylinder is sufficient to withstand this biting force.

Advantageously, the blocking means may include a stud positioned on the bearing means and extending along the longitudinal axis of the device from the proximal face of said bearing means, diametrically opposite the inner face of the separating part.

Advantageously, the blocking means may further include a clasp assuming the form of a straight prism and comprises, in a central part of its volume, a trench forming two longitudinal arms arranged to cooperate with at least one face of the stud.

Advantageously, the clasp may include nonreturn means, said nonreturn means comprising notches positioned one across from the other in the trench of said clasp and arranged to catch on a protruding edge formed at the periphery of the stud.

Advantageously, the clasp may include a straight prism with a triangular base.

Advantageously, at least one of the faces of the stud and/or the clasp is treated so as to have a nonslip property.

The invention also relates to a method for placing a device for maintaining a probe according to one of the preceding claims, said probe already being in place on the patient's body, including the steps consisting of:
Introducing the probe between the proximal end of the blocking means and the guide means,
Causing the probe to penetrate the first radial opening of the bearing means (respectively, the second radial opening of the guide means),
Causing the probe to penetrate the second radial opening of the guide means (respectively, in front of the first radial opening of the bearing means), such that the probe extends along the longitudinal axis of the device.

This method may further include the following steps:
Actuating the blocking means.
Non-invasively fastening the device on the patient's body.

This method is advantageously carried out with only one hand.

In an application to the fastening of an orotracheal probe, the advantages of the device according to the invention are as follows:
It protects the orotracheal probe from any biting,
It takes up a minimal amount of space inside and outside the patient's mouth,
It is easy to use, allowing placement and removal with a single hand (one hand secures the probe, the other hand mobilizes the fastening device),
It is able, in a single declination, to adapt to all existing probe diameters. It is easily possible to provide an adult model and pediatric model.

Embodiments and variants will be described below, as non-limiting examples, in reference to the appended drawings, in which.

Figure 1:
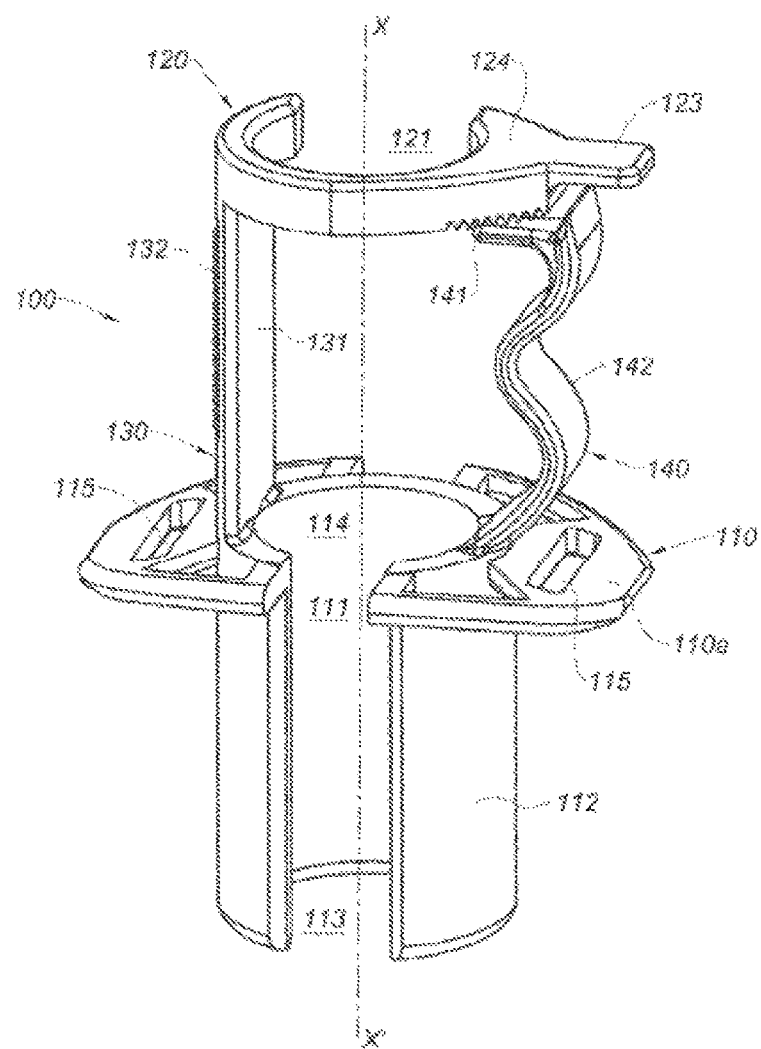
FIGS. 1 and 3 show a perspective view of the device.

The device 100 illustrated in FIGS. 1 to 4 develops around a rectilinear axis X-X'. It is intended to maintain in place and protect a conduit placing the inside of a patient's body in communication with the outside, for example an orotracheal probe, this example not being limiting. When the probe is engaged in the device, it is placed along the axis X-X'.

The device being intended to be applied on a patient's body, it includes a bearing part 110 that extends radially around the axis X-X'; as illustrated, the bearing part 110 assumes the form of a substantially oval corolla, having a distal face 110b intended to come into contact with the skin or lips of the patient and a proximal face 110a opposite. The bearing part 110 is slightly curved, the concave side being turned toward the distal face 110b, i.e., toward the patient during use. The bearing part 110 includes an axial opening 114, for example circular, provided to receive the probe.

This bearing part 110 includes, on the periphery, openings 115 provided to fasten the device on the patient's body, for example using a cord.

The device includes, at its proximal end, a ring 120 that extends radially around the axis X-X', forming guide means for the probe and preventing it from folding or bending toward the proximal face 110a of the bearing part 110 when it is in place. The plane of the bearing part 110 and that of the ring 120 are therefore substantially parallel. The ring 120 includes a protuberance 124 that extends radially in the direction opposite the separating part 130, the distal face 122 of which is notched. The protuberance 124 extends opposite the axis X-X' by a tongue 123.

The bearing part 110 and the ring 120 are secured and maintained at a distance by a separating part 130 that extends longitudinally from the proximal face 110a of the bearing part 110, on the border of its axial opening 114. This separating part 130 assumes the form of an elongated plate, longitudinally rectilinear and having a curved cross-section.

A blocking part 140 also extends from the proximal face 110a of the bearing part 110 toward the ring 120, diametrically opposite relative to the separating part 130. Its longitudinal extension is substantially equal to that of the separating part 130; its proximal end is free. It is intended to block the probe inside the device 100 and will be described in detail later.

The device 100 includes a cylindrical body 112 that extends longitudinally and coaxially from the distal face 110b of the bearing part 110. When the probe is in place in the device, it is placed axially in this cylindrical body 112. The device of these figures is in particular intended to fasten an orotracheal probe, and the function of this cylindrical body is to protect the probe from involuntary biting movements by the patient.

The device 100 includes specific means for allowing easier placement of a probe [whereof] both ends are engaged, the distal end inside the patient's body and the proximal end being connected to an apparatus. To that end, the device includes:

A first radial opening 111 in the bearing part 110, communicating with the axial opening 114 of said bearing part 110, A second radial opening 121 in the ring 120, such that the ring 120 is interrupted, this second radial opening 121 being directly opposite relative to the first radial opening 111.

When the device includes a cylindrical body 112, the latter includes a longitudinal slit 113 in communication with the first opening 111.

The fastening of the device is done as follows:

Force the passage of the probe between the proximal end of the strip 140 and the protuberance 124 by acting on the elasticity of the ring 120 and the separating part; after this manipulation, the axis of the probe is substantially orthogonal to the axis X-X', Pivot the distal part of the probe so as to introduce it into the first radial opening 111, and in the longitudinal slit 113 when the device includes a cylindrical body 112, so as to place it in the axial opening 114 of the bearing part, Pivot the proximal part of the probe so as to introduce the probe into the second radial opening 121, so as to align it along the axis X-X' of the device.

Of course, the last two operations can be done in the opposite order.

It is important to note that these operations can be done with a single hand by the caregiver, which is a major advantage relative to the devices of the state of the art.

Once the device is in place on the probe, it can slide freely on the probe without any risk of falling and can be placed by the caregiver in the anticipated location on the patient's body. From there, it suffices to avoid a longitudinal movement relative to one another. To that end, the device includes means for blocking the probe inside the device, in particular in the form of the blocking part 140.

As illustrated in the figures, the blocking part is a strip 140 that has a corrugated shape, in particular including a "hollow part" 142, i.e., closer to the axis X-X' of the device. This hollow part 142 is intended to form a bearing for the operator's finger when he presses the strip 140.

Figure 2:
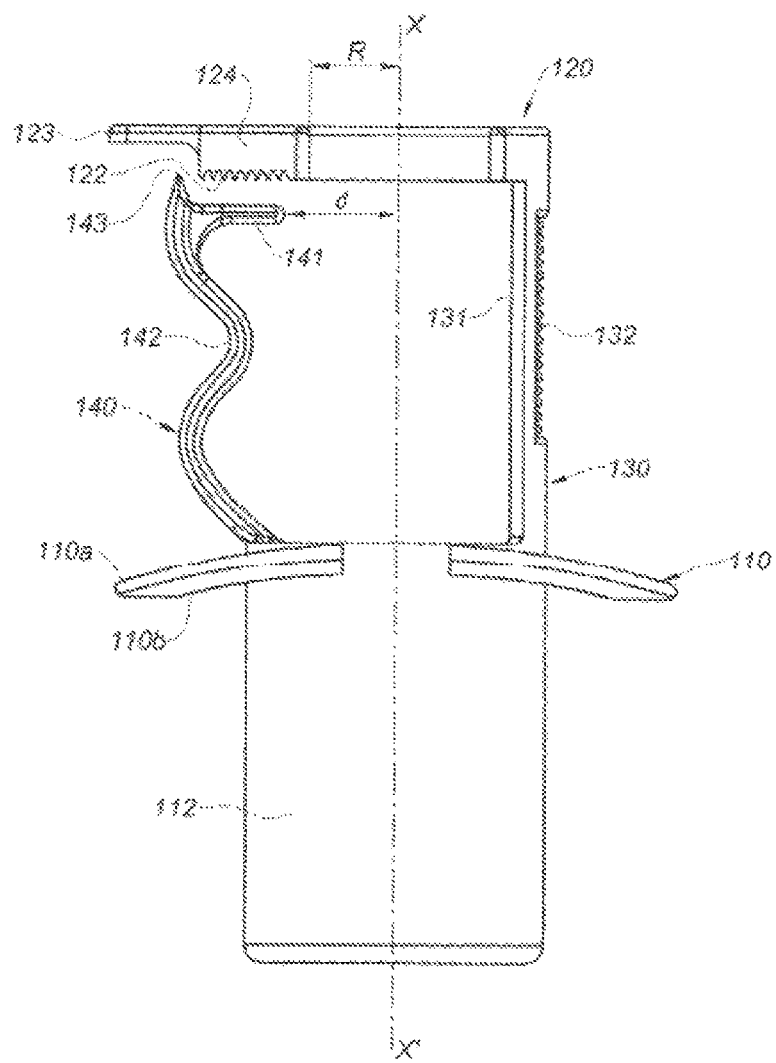
FIG. 2 shows an elevation view of the device.
Figure 3:
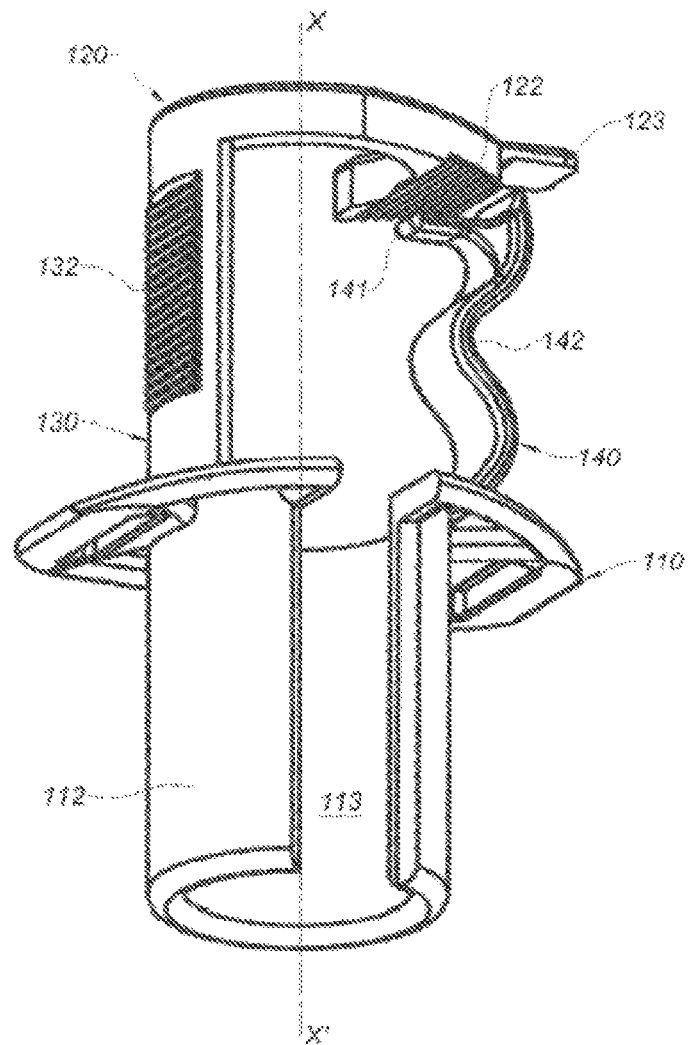

At its proximal end, the blocking part 140 includes a protuberance 141 forming a blocking part that extends toward the axis X-X' of the device, assuming the form of a nose. This protuberance 141 is provided to come into contact with the probe to block it inside the device. In the equilibrium position of the blocking part 140, as illustrated in FIG. 2, for example, the distance d between the end of the nose and the axis X-X' is greater than the radius R of the ring 120, such that it does not exert any force on the probe when it is present in the device.

In light of its position diametrically opposite the separating part 130, it will be understood that when the operator presses on the strip 140, the probe is blocked by friction between the protuberance 141 and the inner face 131 of the separating part 130.

In practice, the operator, with two fingers of a same hand, presses on the outer face of the separating part 130 and the outer face of the blocking part 140, like a clamp. To facilitate this operation, as set out above, the outer face of the blocking part 140 includes a hollow part 142; furthermore, the outer face of the separating part 130 includes a series of slots 132 provided to prevent the finger from sliding.

Preferably, the separating part 130 is more rigid than the blocking part 140, for example because it has a section and/or width larger than that of the blocking part 140. In this way, during pinching of the device, it is preferably the blocking part 140 that bends.

To ensure better blocking of the probe, the inner face 131 of the separating part 130 can be configured or treated so as to have a nonslip property.

The device further includes nonreturn means for the blocking means. To that end, the proximal end of the blocking part 140 includes a tooth 143 provided to cooperate with the notches of the distal face 122 so as to form a nonreturn means; the notches are for example asymmetrical.

When the tooth 143 is engaged in the notches of the distal face 122 following pressure exerted by the user, the blocking part 140 is maintained in its bent position and the operator can release the device.

When he wishes to release the probe, the operator exerts a force on this tongue 123 opposite the blocking part 140, such that the tooth 143 is freed from the notches of the distal face 122 and, by elasticity, the blocking part 140 returns to its equilibrium position, where it is separated from the axis X-X' and therefore the probe.

Figure 4:
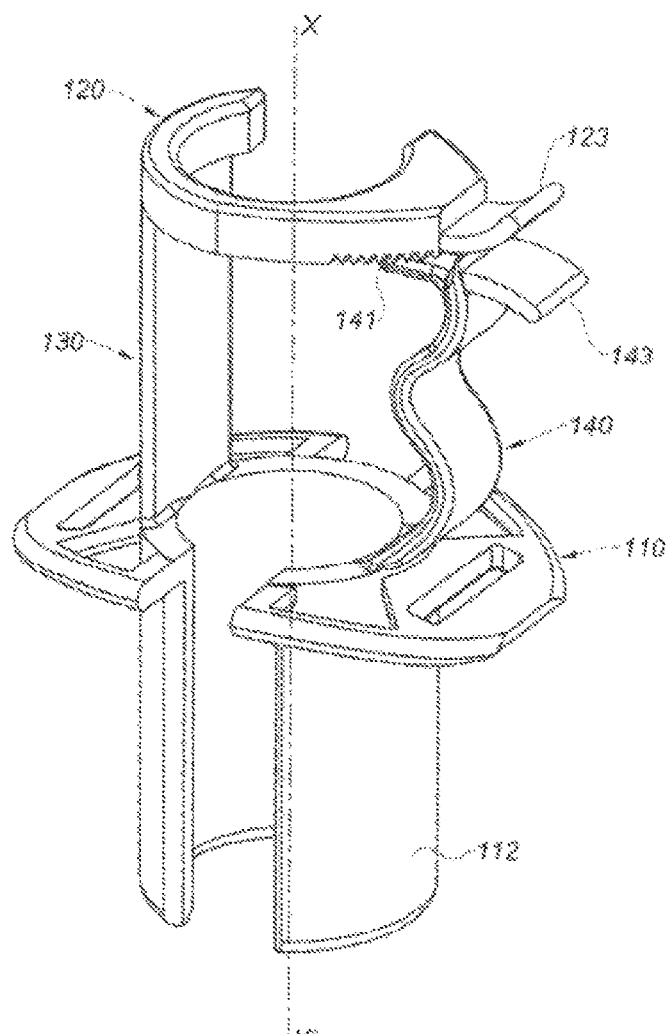
FIG. 4 shows a variant of the device in perspective view.

In the variant illustrated in FIG. 4, the blocking part 140 also includes a tongue 143 at its proximal end, which extends opposite the protuberance 141. The two tongues 123 and 143 are curved and extend radially while moving away from one another so as to facilitate the insertion of the probe between the blocking part 140 and the ring 120.

It is important to note that the device is not provided, like some devices of the state of the art, to interrupt the circulation of a liquid or gaseous fluid in the probe. It is even intrinsically provided so that such an interruption, which could, after a manipulation error, have extremely serious consequences, is impossible. Indeed, if the operator were to exert an excessive pinching force that would result in the probe being crushed between the protuberance 141 and the inner face 131 of the separating part, the blocking part 140, once released, would again become engaged with the notches of the distal face 122.

It emerges from the above description that the device is in a single piece, which allows it to be placed with one hand. Furthermore, this avoids risks of separation and lost parts. The device may be made by injection molding.

This description is not limiting. Thus:
- The bearing part could assume another form, for example circular, polygonal, or even a form of branches radiating around the axis X-X',
- The ring of the guide means could assume a form other than circular, for example oval or polygonal,
- The separating part 130 could be planar,
- The first and second radial openings 111, 121 could be longitudinally aligned and not diametrically opposite; the placement of the device on the probe would be easier as a result, but the risks of unwanted separation would be increased,
- If the first and second radial openings 111, 121 are longitudinally aligned and not diametrically opposite, the step for relative pivoting of the device and the probe does not take place,
- The blocking part 140 may not be corrugated, and may in particular be rectilinear or simply curved,
- The protuberance 141 may assume a form other than that of a nose; it may have the form of a pad, thereby increasing the friction effect against the probe.

Figure 5:
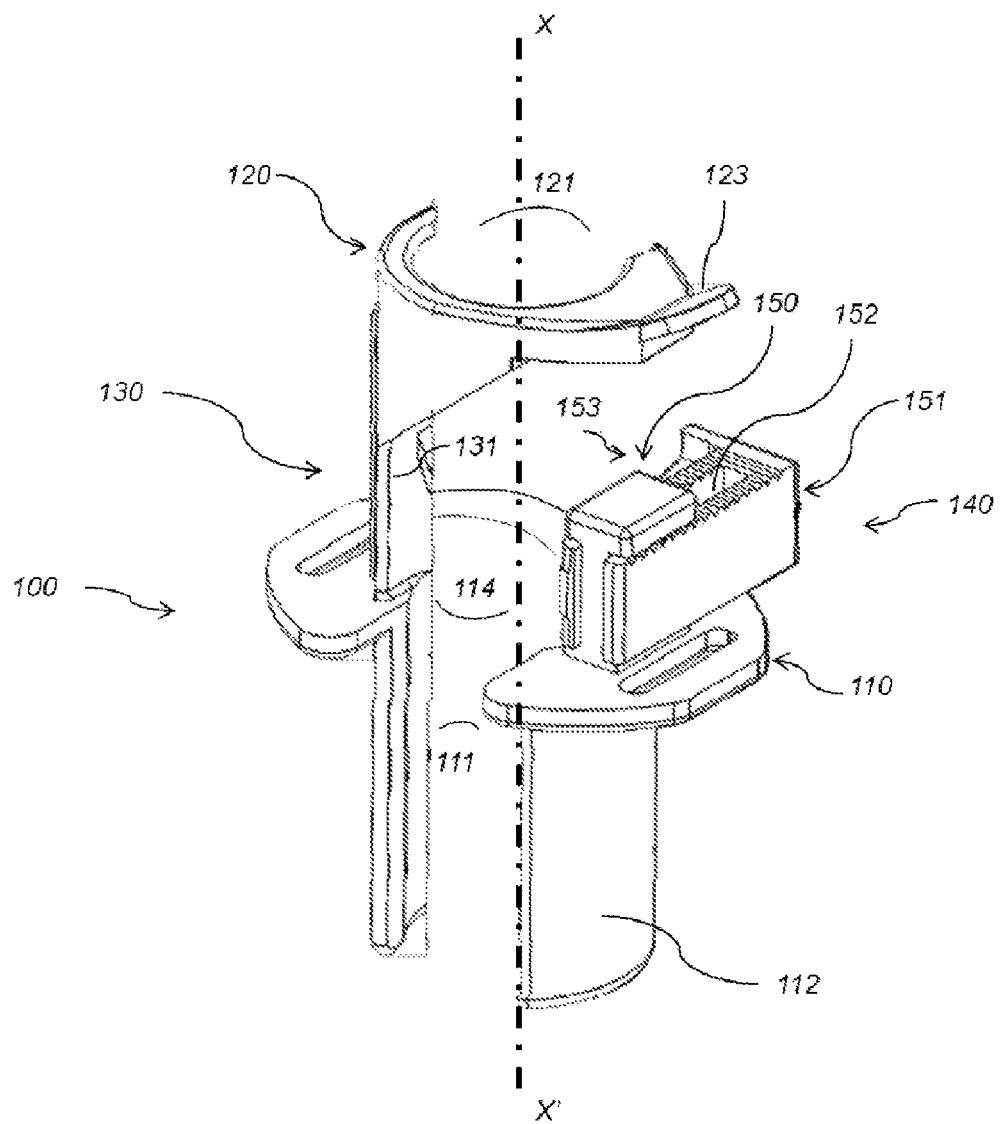
FIG. 5 shows a variant of the device in perspective view.

As illustrated in FIG. 5, an example embodiment according to the invention comprises a blocking means 140, said blocking means including a stud 150 positioned on the bearing means 110 and extending along the axis X-X' from the proximal face of said bearing means, diametrically opposite the inner face 131 of the separating part 130. The blocking means 140 may further include a clasp 151 intended to slide along the stud 150.

According to one example embodiment of the invention, the clasp 151 is in the form of a straight prism, for example a regular rhomb. The clasp 151 comprises, in a central part of its volume, a trench 152 with a given length, extending along a longitudinal axis of said clasp and forming two longitudinal arms. Said two longitudinal arms are intended to be inserted around side faces of the stud 150. In particular, said two longitudinal arms are provided to cooperate with the faces of the stud 151 so as to guide the clasp 150 for its placement along the bearing means 110 up to a final fastening position, in which the clasp becomes secured to said bearing means, and the device 100.

When the clasp 151 is slid, for example partially, along the stud 150, the blocking means 140 makes it possible to block a probe whereof both ends are engaged, to maintain said probe in the device 100. In light of its diametrically opposite position with respect to the separating part 130, it will be understood that when the clasp 151 is slid along the stud 150, said probe is blocked by friction between the inner face 131 of the separating part 130 and an inner side face 153 of the clasp 150.

According to one example embodiment of the invention, the clasp 151 includes a straight prism with a triangular base. According to this example, the sliding of the clasp 151 along the stud 150 makes it possible to exert gradual lateral pressure on a probe inserted into the device 100 along the axis X-X', based on the length of said clasp that is slid along said stud. Indeed, a clasp 151 comprising a straight prism with a triangular base makes it possible to gradually modify the size of the axial opening 114 of the device 100 once a clasp is slid along the stud 150. The quality of the blocking of a probe in the device 100 can thus be adapted as a function of the diameter of the probe inserted into said device. In particular, the blocking of a probe with a small diameter or large diameter may be ensured by more or less significant sliding of the clasp 150 along the stud 150.

According to one example embodiment of the invention, the upper base of the stud 150 further includes a face that extends along the bearing means 110 and the width of which is larger than the separation of the longitudinal arms of the trench 152 of the clasp 151. In particular, the stud 150 is an L-shaped block, the central part of which is intended to cooperate with the clasp 151. This makes it possible to ensure the blocking of the clasp 151 in a direction parallel to the axis X-X' once a clasp is slid at least partially along the stud. Under the application of a sufficient pressure exerted by the user, the clasp 151 can also be moved in a return movement to free a probe engaged in the device 100. Advantageously, the operator can, with one or two fingers of a same hand, press on the clasp 150 to cause it to slide longitudinally along the stud 151. When he wishes to release the probe, the operator exerts a force on the clasp 151 to slide it and release the notches of the side faces of the stud 150. The blocking means 140 is thus moved away from the axis X-X' and therefore from the probe. To ensure better blocking of the probe, at least one of the faces of the clasp 151 and/or the stud 150 can be treated so as to have a nonslip property.

According to one example embodiment of the invention, the clasp 151 further includes nonreturn means. According to this example embodiment, these nonreturn means comprise notches arranged in the trench 152 of the clasp 151, and arranged to catch on the protruding edge formed on the periphery of the stud 150. Advantageously, these notches allow better fastening of the clasp 151 when the latter is slid over a predetermined length of a side surface of said stud. To that end, the two inner faces of the trench 142 of said clasp each include at least one notch provided to cooperate with one of the faces of the stud 151, so as to form a nonreturn means. Advantageously, the notches are positioned across from one another in the trench 152. The cooperation of these notches with the side faces of the stud 150 makes it possible to prevent a longitudinal return movement of the clasp.

The invention claimed is:

1. A device for maintaining a probe placing the inside of a patient's body in communication with the outside, characterized in that it comprises, arranged along a longitudinal axis of the device:
    at a distal end, a bearing means of the device configured to contact the patient's body that extend radially, including an axial opening for a passage of said probe and including a first radial opening communicating with said axial opening,
    at a proximal end, a guide means for said probe including a second radial opening,
    a longitudinal separating means for said bearing means and said guide means,
    wherein said separating means comprising a separating part assuming the form of an elongated plate that is longitudinally rectilinear and extends longitudinally from the bearing means to the guide means, said separating part having a curved cross-section, said curved cross-section extending partially around the longitudinal axis.

2. The device for maintaining a probe according to claim 1, wherein the first radial opening and the second radial opening are substantially diametrically opposite relative to the longitudinal axis of the device.

3. The device for maintaining a probe according to claim 1, wherein the bearing means includes fastening elements provided to fasten the device on the patient's body.

4. The device for maintaining a probe according to claim 1, wherein the bearing means comprising a distal face, wherein a coaxial cylindrical body extends from the distal face, including a longitudinal slit, said slit being in communication with the first radial opening of the bearing means.

5. The device for maintaining a probe according to claim 1, wherein the guide means includes a protuberance that extends radially in a direction opposite the separating part.

6. The device for maintaining a probe according to claim 5, wherein the guide means includes a tongue that extends radially from the protuberance.

7. The device for maintaining a probe according to claim 1, wherein the device further includes a blocking means provided to block the probe against the separating means when said probe extends along the longitudinal axis of the device.

8. The device for maintaining a probe according to claim 7, wherein the blocking means includes a strip that extends longitudinally from a proximal face of the bearing means, diametrically opposite the separating means.

9. The device for maintaining a probe according to claim 8, wherein the strip has a radially curved shape and includes a protuberance that extends toward the longitudinal axis of the device, so as to block the probe between a blocking part and the separating means when force is exerted on said strip.

10. The device for maintaining a probe according to claim 7, wherein an inner face of the separating means is provided with a nonslip layer.

11. The device for maintaining a probe according to claim 7, wherein the device further includes nonreturn means between the blocking means and the guide means providing engagement between the blocking means and the guide means and thereby preventing a return of the blocking means into a position where a protuberance, which extends from the blocking means toward the longitudinal axis of the device, is brought closer to the separating part.

12. The device for maintaining a probe according to claim 11, wherein the nonreturn means includes a notched surface on a distal face of the protuberance, said notched surface being provided to cooperate with a tooth situated at proximal end of the blocking means.

13. The device for maintaining a probe according to claim 7, wherein the device is formed in a single piece.

14. The device for maintaining a probe according to claim 7, wherein the blocking means includes a stud positioned on the bearing means and extending along the longitudinal axis of the device from a proximal face of said bearing means, diametrically opposite an inner face of the separating part.

15. The device for maintaining a probe according to claim 14, wherein the blocking means further includes a clasp assuming a form of a straight prism and comprises, in a central part of its volume, a trench forming two longitudinal arms arranged to cooperate with at least one face of the stud.

16. The device for maintaining a probe according to claim 15, wherein the clasp includes nonreturn means, said nonreturn means comprising notches positioned one across from the other in the trench of said clasp and arranged to catch on a protruding edge formed at a periphery of the stud.

17. The device for maintaining a probe according to claim 15, wherein at least one of the faces of the stud and/or the clasp is treated so as to have a nonslip property.

18. The device for maintaining a probe according to claim 8, wherein the device is made from a plastic for pharmaceutical or medical-surgical use.

19. A method for placing a device for maintaining a probe according to claim 1, said probe already being in place on the patient's body, including the steps consisting of:
    Introducing the probe between a proximal end of a blocking means and the guide means, and then either:
    Causing the probe to penetrate the first radial opening of the bearing means, and
    Causing the probe to penetrate the second radial opening of the guide means, or alternatively:
    Causing the probe to penetrate the second radial opening of the guide means, and
    Causing the probe to penetrate the first radial opening of the bearing means;
    such that the probe extends along the longitudinal axis of the device.

20. The method for placing a device for maintaining a probe according to claim 19, said device including the blocking means provided to block the probe against the longitudinal separating means, wherein the method includes the step consisting of:
    Actuating the blocking means.

21. The method for placing a device for maintaining a probe according to claim 19, wherein the method includes the step consisting of:
    Non-invasively fastening the device on the patient's body.

22. The method for placing a device for maintaining a probe according to claim 19, wherein the method is carried out with only one hand.

23. The device for maintaining a probe according to claim 15, wherein the clasp includes a straight prism with a triangular base.

* * * * *